United States Patent [19]

Rittel et al.

[11] 3,948,876

[45] Apr. 6, 1976

[54] PROCESS FOR THE PURIFICATION OF SYNTHETIC CALCITONINS

[75] Inventors: Werner Rittel, Basel; Max Brugger, Birsfelden; Bernhard Riniker, Frenkendorf, all of Switzerland

[73] Assignee: Ciba-Geigy Corporation, Ardsley, N.Y.

[22] Filed: Dec. 3, 1974

[21] Appl. No.: 529,195

[30] Foreign Application Priority Data

Dec. 14, 1973 Switzerland.................. 17550/73

[52] U.S. Cl............................................. 260/112.5 T
[51] Int. Cl.² C07C 103/52; C07G 7/00; C08H 1/00
[58] Field of Search................... 260/112.5, 112.5 T

[56] References Cited
UNITED STATES PATENTS

| | | | |
|---|---|---|---|
| 3,749,703 | 7/1973 | Guttmann et al.............. | 260/112.5 |
| 3,775,394 | 11/1973 | Arnaud........................... | 260/112.5 |

OTHER PUBLICATIONS

Tenenhouse et al., Proc. Nat. Acad. Sci., 53, pp. 818–822 (1965).

Tashjian et al., Am. J. Med., 43, pp. 668–677 (1967).

*Primary Examiner*—Lewis Gotts
*Assistant Examiner*—Reginald J. Suyat
*Attorney, Agent, or Firm*—Joseph G. Kolodny; John J. Maitner; Theodore O. Groeger

[57] ABSTRACT

Peptides of the calcitonin type when obtained by synthesis can be purified in a simple manner by forming inner salts, which precipitate from aqueous solutions of salts of the peptides with acids or bases when these solutions are adjusted to the isoelectric range. Impurities remain in solution, while the inner salts separate practically quantitatively. The precipitation is completed after several hours. The peptides can then be recuperated by treatment with an acid, especially a therapeutically suitable acid. The process affords products which are superior to those obtained by purification methods hitherto known and gives higher yields. Other long-chain peptides such as ACTH, insulin or glucagon cannot be purified in this manner.

9 Claims, No Drawings

PROCESS FOR THE PURIFICATION OF SYNTHETIC CALCITONINS

In the synthetic manufacture of long-chain peptides from peptide fragments, there are generally formed, to a lesser or greater degree, considerable amounts of byproducts which are difficult to separate. Thus, in the amino acid chain certain amino acid radicals can be present in the form of diastereomers; for example, in the case of the synthesis of human calcitonin, described by Sieber et al. [Helv. Chim. Acta 53, 2135–2150 (1970)], the amino acid radicals $Leu^4$, $Leu^9$, $Thr^6$, $Phe^{16}$ and $His^{20}$. Furthermore, there can occur in the case of sulphur-containing peptides an alkylation or an N → O- acyl migration, as likewise described in the stated publication. In order to remove such by-products, there are carried out, at the stage of larger protected fragments and/or at the stage of the protected total peptide and/or in the final product itself, costly purification operations, such as counter-current distribution, electrophoresis or chromatography. These operations render the manufacture of such long-chain peptides on a commercial scale more difficult, for large quantities of adsorbents and/or solvents are required, and these are difficult and costly to recover.

There has now been found a very simple purification process for peptides of the calcitonin type having an isoelectric point lying between the pH values of about 5 to 10 (i.e. pI = approx. 5 – 10). The process of the invention is characterised in that the calcitonin peptide is precipitated as inner salt from an aqueous solution of a salt with acids or bases or bases by adjustment of the pH to the isoelectric range. The expression isoelectric "range" is used since, in the case of the present compounds, the isoelectric point is not sharply defined but extends over a fairly wide pH range, cp. Kortum, Lehrbuch der Electrochemie, Verlag Chemie, Weinheim, 1966, p. 336. By isoelectric range is understood the pH range of pI ± approx. 1 pH unit.

Surprisingly, the peptide obtained by this mode of precipitation has a high degree of purity, since the above-mentioned by-products are not coprecipitated or, in the case of the O-acyl derivatives, are converted back into the N-acyl derivatives. The degree of purity of the products exceeds that of the peptides purified twice by counter-current distribution, namely at the stage of the protected intermediates and in the final product (cp. e.g., Helv. Acta 53, 2135 (1970)). Calcitonins of high purity are obtaned also in the case where the protected intermediate (protected dotriacontapeptideamide) has been purified not by counter-current distribution, etc., but only by dissolving and reprecipitation. The losses as a result of the purification operations are less than those in the customary processes. The resulting product exhibits full biological activity.

The method was not to be anticipated, for other long-chain peptides, such as ACTH, insulin, glucagon, cannot be purified in this manner.

Peptides of the calcitonin type having an isoelectric point of pI = approx. 5 – 10 are, in particular: the human calcitonin (calcitonin M) and derivatives and analogs thereof, for example, those that are described in the Belgian Patent Specifications No. 737,890, No. 740,256, No. 757,786 and in the Belgian Patent Specification 812,881. Analogs are, in particular, those containing, instead of methionine[8], an α-lower-alkyl-α-aminoacetic acid, especially one wherein lower alkyl has 2–4 carbon atoms, particularly valine, also norvaline, leucine, isoleucine, norleucine or α-aminobutyric acid. Further preferred exchange amino acids which may be present in addition to the mentioned exchange amino acids in the 8-position are: L-lysine[11], L-leucine[12], L-leucine[16], L-leucine[19], L-tyrosine[22], L-asparagine[26] and L-threonine[27]. Derivatives are, in particular, corresponding desamino[1]-peptides as well as $N^\alpha$-acyl derivatives.

Acyl groups for acylation of the $N^\alpha$-amino group are the radicals of carboxylic acids such as aliphatic, aromatic, araliphatic, heterocyclic and heterocyclyl-aliphatic carboxylic acids, especially of lower monobasic or dibasic alkanoic or alkenoic acids, particularly lower alkanoic acids having 1–4 carbon atoms, such as formic acid, acetic acid, propionic acid and butyric acids, and also acrylic acid and succinic acid, of alicyclic carboxylic acids such as cycloalkylcarboxylic acids, such as unsubstituted and substituted benzoic acid or phthalic acid, of unsubstituted and aryl-substituted aryl-lower-alkyl- or alkenylcarboxylic acids such as phenylacetic acid, of unsubstituted or substituted monobasic or dibasic 5-membered to 6-membered heterocyclic acids with nitrogen, sulphur and/or oxygen as hetero atoms, such as pyridinecarboxylic acids and thiophenecarboxylic acids, or of heterocyclyl-lower alkanoic acids, such as pyridylacetic acid, imidazolylacetic acid, wherein the substituents of the rings are, for example, halogen atoms, nitro groups, lower alkyl groups or lower alkoxy groups or lower carbalkoxy groups. Further acyl radicals to be mentioned are, in particular, acyl radicals of amino acids, especially of α-amino acids, such as glycyl; L-leucyl, L-pyroglutamyl, also acyl radicals which are derived from carbonic acid or thiocarbonic acid or their esters or amides, for example, lower alkoxycarbonyl groups, such as ethoxycarbonyl and tert.-butoxycarbonyl, also unsubstituted benzyloxycarbonyl and benzyloxycarbonyl substituted as indicated above, carbamoyl and thiocarbamoyl as well as N-substituted carbamoyl and thiocarbamoyl, for example, N-lower-alkylcarbamoyl, N-phenylcarbamoyl and N-phenyl-thiocarbamoyl.

The human calcitonin has an isoelectric range of 7–8. The shift of the isoelectric range on replacement of certain amino acids by others can be experimentally determined, for example, electrophoretically, or it can be calculated. The isoelectric point of peptides can be calculated, for example, according to J. Greenstein and M. Winitz "Chemistry of the Amino Acids", Vol. 1, Ed. John Wiley & Sons, Inc., New York, London, 1961, p. 482 and following.

Suitable salts of peptides, which can be used as starting material in the new process, are all salts that are soluble in water or, optionally, in a solution of water and an organic peptide solvent, for example, lower alkanols, especially methanol, ethanol, isopropanol, tert.-butanol or dimethylformamide or dimethylacetamide. Such salts are, e.g., salts of mineral acids, particularly hydrohalic acids, or of organic acids, especially acetic acid and halogenated acetic acids such as trifluoroacetic acid or dichloroacetic acid, also sulphonic acids such as lower-alkanoic sulphonic acids, for example, methanesulphonic acid, or benzenesulphonic or toluenesulphonic acids. The peptide can also be employed as salt with bases, for example, with ammonia or with primary, secondary, tertiary or quaternary amines, e.g., corresponding amines containing as organic radicals one or more lower alkyl, cycloalkyl (having preferably 5–6 ring atoms) or aralkyl radicals, particularly phenyl-loweralkyl radicals, e.g., triethylamine, cyclohexylamine, dicyclohexylamine, benzylamine or trimethylbenzylammonium hydroxide, also with guanidine substituted by the organic radicals mentioned, e.g., tetramethylguanidine. The peptide is above all used in the form of the salt which is obtained in a particular synthesis, for example, in the form of the hydrochloride, the hydrobromide, the hydrofluoride, the trifluoroacetate or the acetate. If desired, the salts, in the form of which the peptide is obtained, can be converted into the acetic acid salt before the purification operation, for example, by means of ion exchangers.

The salt is dissolved in water or in an aqueous solution of an organic peptide solvent. The pH is measured and, depending on whether there is present a salt with an acid or with a base, base or acid is carefully added until the isoelectric range is attained. As bases there are used, for example, ammonia, aqueous alkali, especially sodium hydroxide solution or potassium hydroxide solution, alkali carbonates or alkali hydrogen carbonates, e.g., sodium carbonate or sodium bicarbonate, organic bases such as the abovementioned amines, or preferably basic ion exchangers. Suitable ion exchangers are weakly basic ones, those of medium basicity, and strongly basic ones. Such ion exchangers can be obtained by polymerisation of suitable parent substances or by introduction of basic groups into polymers. It is advantageous to use products obtainable commercially, for example, products based on cellulose, such as DEAE Cellulose or DEAE Sephadex, Particularly suitable ion exchangers are those based on polystyrene, which are marketed by various firms under different trade names, e.g., the weakly basic Merck ion exchanger No. II, or the strongly basic Merck ion exchanger No. III, or the various commercial forms of the basic Dowex ion exchangers or of the basic Amberlites. If the isoelectric range is to be attained by acids, then there are used, for example, mineral acids, above all hydrohalic acids, especially hydrochloric acid, or organic acids, e.g. acetic acid or citric acid, or acid ion exchangers corresponding to the above-mentioned basic ion exchangers, e.g., those based on polystyrene, such as "Amberlite" IR-120 or "Dowex" 50.

Whe the isoelectric range is attained, there slowly commences the precipitation of the peptide. The precipitation process is allowed to proceed for several hours, e.g., for two hours, until it is completed. During this period of time, the pH value increases by about one unit. Thus, for example, the pH of calcitonin M-acetate is approx. 4. On addition of weakly basic ion exchanger, it rises slowly to 6.0 to 6.2: the precipitation commences at this point. In the course of a further 2 hours, the pH increases to about 7.5, and then remains constant.

After the complete precipitation of the peptide, it is separated, for example, by filtration with suction or by centrifuging, and subsequently thoroughly washed with water. Since the precipitated peptide is very difficultly soluble in water, there occur in the process practically no losses. If precipitation has been effected by addition of ion exchangers, then the free peptide has to be separated from the ion exchanger. This can be performed, for example, by a process in which the peptide is converted by means of an acid into a desired salt, e.g., into the acetate or hydrochloride, and the solution is separated from the ion exchanger, e.g., by normal filtration or by filtration with suction, and then lyophilised. If the procedure has not entailed the use of an ion exchanger, then, if desired, the precipitated product can be converted into the required salt form by dissolving in acid and lyophilising.

Acids suitable for the formation of therapeutically usable salts are, for example, inorganic acids, such as hydrohalic acids, for example, hydrochloric acid or hydrobromic acid, perchloric acid, nitric acid or thiocyanic acid, sulphuric or phosphoric acid; or organic acids, such as formic acid, acetic acid, propionic acid, glycolic acid, lactic acid, pyruvic acid, oxalic acid, malonic acid, succinic acid, maleic acid, fumaric acid, malic acid, tartaric acid, citric acid, ascorbic acid, hydroxymaleic acid, dihydroxymaleic acid, benzoic acid, phenylacetic acid, 4-aminobenzoic acid, 4-hydroxybenzoic acid, anthranilic acid, cinnamic acid, mandelic acid, salicylic acid, 4-aminosalicylic acid, 2-phenoxybenzoic acid, 2-acetoxybenzoic acid, methanesulphonic acid, ethanesulphonic acid, hydroxyethanesulphonic acid, benzenesulphonic acid, p-toluenesulphonic acid, naphthalenesulphonic acid or sulphanilic acid.

The peptides obtained by the process of the invention can be used in the form of pharmaceutical preparations. These contain the peptides in admixture with a pharmaceutical, organic or inorganic carrier substance that is suitable, for example, for the intravenous, intramuscular, subcutaneous or intranasal administration. Suitable substances are those that do not react with the polypeptides, such as, gelatine, agar-agar, tragacanth, cellulose, for example, "Avicel" (microcrystalline cellulose) and cellulose derivatives, such as carboxymethylcellulose, cellulose ethers such as methylcellulose or ethylcellulose, polyalkylene glycols, such as propylene glycols, water, monohydric or polyhydric alcohols such as ethanol, isopropanol, glycerol and hexitol, vegetable oils and other fatty acid esters such as groundnut oil, cottonseed oil, almond oil, olive oil, castor oil, ethyl oleate, isopropyl myristate, isopropyl palmitate, "Cetiol V" (oleic acid esters of liquid fatty alcohols), "Miglyol" or "Labrafac" (triglyceride mixture of fatty acids having 8–12 carbon atoms), "Labrafil M 2735" or "Labrafac WL 1219" (mixtures of glycerol and polyoxyethylene fatty acid esters), "Arlacel" (sorbitane fatty acid esters), "Tween" (Polyoxyethylene sorbitane monooleate), silicone oils such as dimethylsilicone oil, or other known medicinal excipients. The pharmaceutical preparations can be, for example, in the form of a lyophilisate, or they can be in liquid form as solutions, suspensions, emulsions or sprays; see, for example, the German Offenlegungsschrift No. 2,212,315. They are optionally sterilised and/or contain auxiliaries, such as preservatives, stabilisers, wetting agents or emulsifiers. They may also contain other therapeutically valuable substances.

The invention is described in the following examples. The temperature values are given in degrees Centigrade.

The following systems are used in the thin-layer chromatographical procedure:
System 43C: tert.amyl alcohol/isopropanol/water (51:21:28);
System 45: sec. butanol/3% aqueous ammonia (70:30);
System 52: n-butanol/glacial acetic acid/water (75:7.5:21);
System 52A: n-butanol/glacial acetic acid (67:10:23);

System 70: ethyl acetic/pyridine/water (40:20:40), upper phase;
System 79: n-butanol/pyridine/water (34:33:33);
System 96: sec.-butanol/glacial acetic acid/water (67:10:23);
System 100: ethyl acetate/pyridine/glacial acetic acid/water (62:21:6:11);
System 101A: n-butanol/pyridine/glacial acetic acid/water (42:24:4:30);
System 102A: ethyl acetate/methyl ethyl ketone/formic acid/water (50:30:10:10);
System 107: ethyl acetate/pyridine/water (49:24:27);
System 114: sec.butanol/methyl ethyl ketone/25% aqueous $NH_3$/water (37:37:13:13);
System 121: isopropanol/25% aqueous $NH_3$/water (70:10:20);
System 121A: isopropanol/25% aqueous $NH_3$/water (85:5:10);
DS: On silica gel ready-prepared plates SL 254 of Antec, Birsfelden.
DC: On ready-prepared cellulose plates of Merck, Darmstadt.
DA: On Alox plates (45 g of $Al_2O_3$ of Camag, Muttenz, + 3.5 g of gypsum, thickness 0.3 mm).

The following abbreviations are used in the Examples:
Boc tert.-butoxycarbonyl,
Z carbobenzoxy,
OtBu tert.-butyl ester,
ONp p-nitrophenyl ester,
OMe methyl ester,
OSu hydroxysuccinimide ester,
tBu tert.-butyl ether,
DMF dimethylformamide.

EXAMPLE 1

Pure calcitonin M-acetate 50 mg of crude trifluoroacetic acid salt of calcitonin M (Belgian Patent Specification 737,890) is dissolved in 5 ml of water. The pH value of the solution is 2.5. There is added with stirring in the course of 15 minutes, in several portions, a total amount of 0.6 ml of Merck ion exchanger No. II, weakly basic, free base form; and the pH value increases to 6.2. Stirring is continued for 30 minutes at room temperature, in the course of which the pH value rises to 7.5 and a flaky precipitation occurs. After 3 hours' stirring, the precipitate and ion exchanger are filtered off under suction and subsequently washed with water. The washing water contains 12 mg of byproducts of calcitonin M.

The precipitated calcitonin M is separated from the ion exchanger by the material being washed four times with 4 ml of 90% acetic acid each time, and being filtered each time under suction. The combined acetic acid extracts are lyophilised to obtain 36 mg of calcitonin M in the form of acetic acid salt. The product gives the following analytical data:

| | |
|---|---|
| water content according to Karl Fischer: | 8.1%; |
| acetic acid content (gas-chromatographically): | 1.1%; |
| peptide content: | 89.0%; |
| fluorine content (microanalytical): | 0.02%; | amino acid analysis (6-N. HCl, 24h, 110°) all amino acids in the correct molar ratio, except Ser, Thr, Cys, which are partially decomposed during hydrolysis);

UV spectrum (in 10% acetic acid): $\lambda_{max} = 275$ nm, = 1540.

EXAMPLE 2

Pure calcitonin M-trihydrochloride

1. Calcitonin M-trifluoroacetate (crude).

58.0 g of Boc-Cys-Gly-Asn-Leu-Ser(tBu)-Thr(tBu)-Cys-Met-Leu-Gly-Thr(tBu)-Tyr)tBu)-Thr(tBu)-Gln-Asp(OtBu)-Phe-Asn-Lys(Boc)-Phe-His-Thr(tBu)-Phe-Pro-Gln-Thr(tBu)-Ala-Ile-Gly-Val-Gly-Ala-Pro-$NH_2$ (14.3 mMol) is dissolved under nitrogen in 700 ml of trifluoroacetic acid (85%). This solution is allowed to stand for 2 hours at 30°. It is subsequently stirred into 6 litres of peroxide-free ether, with good ice-cooling. The precipitate is filtered off, washed with ether and dried in high vacuum. There is obtained crude trifluoroacetate of calcitonin M as a colourless powder.

2. Calcitonin M-inner salt.

43.5 g of the crude trifluoroacetate of calcitonin M obtained under 1. is dissolved in 1 litre of 1% acetic acid, filtered through a G-4 glass suction filter, and precipitated with ammonia as follows: the solution is stirred under nitrogen at room temperature, with the pH value being continuously measured with a glass electrode. There is slowly added dropwise approx. 1N ($t = 0.97$) ammonia solution so that after 1.25 hours a pH value of 5 is attained. Within about one further hour, the pH value is raised to 6 by the uniform addition of a further amount of the approx. 1N ammonia solution, whereupon the inner salt of calcitonin M commences to precipitate out as an insoluble powder. The slow addition of ammonia solution is continued until, in the course of approx. one further hour, the pH value has reached 7.6. Stirring is subsequently maintained for 3 hours with scarcely no further change in the pH value occurring. The whole is then filtered, washed with diluted ammonia of pH 7.6 and dried in high vacuum. The yield is 18.9 g of a water-insoluble powder. The gas-chromatographical determination of acetic acid in a sample thus obtaned gives a value of 0.3 per cent by weight of acetic acid (corresponding to approx. 0.17 mol-%).

3. Calcitonin M-trihydrochloride.

27.3 g (8.0 mMol) of calcitonin M-inner salt is suspended in 700 ml of t-butanol. There are added 250 ml of water and 360 ml of 0.1N hydrochloric acid (36 mMol); stirring is carried out for several minutes, and the cloudy solution is subsequently filtered through a G-4 glass suction filter. The filtration residue is dissolved in a further 250 ml of water, and is filtered to the first filtrate. This is frozen and lyophilised. After equilibration with the humidity in the atmosphere there is obtained 27.0 g of calcitonin M-trihydrochloride. The product yields the following analytical data: thin-layer chromatogram on cellulose (Merck):

Thin-layer chromatogram on cellulose (Merck):
Rf = 0.61 in the system 101A
0.52 in the system 45
0.51 in the system 114
on aluminium oxide with 8% gypsum
0.72 in the system 79.

In thin-layer electrophoresis there appears a spot having a migration distance of 4.8 cm in the direction of the cathode, on cellulose plates (Merck) and at pH 1.9; 9 V/cm and 3.5 hours running time.

| | |
|---|---|
| acetic acid content (gas-chromatographically) | <0.05% |
| water content according to Karl-Fischer | 8.5 % |
| chlorine content | 2.80% cal. on anhydrous trihydrochloride 3.02%) |

UV (in 10% acetic acid) : $\lambda_{max} = 275$ nm, $\epsilon = 1440$

The starting material used in Examples 3, 4 and 5 can be produced as described in the German Offenlegungsschrift No. 2,413,106 (corresponding to the Belgian Patent Specification No. 812,881).

EXAMPLE 3

Pure Asn²⁶-Thr²⁷-calcitonin M-trihydrochloride

1. Asn²⁶-Thr²⁷-calcitonin M - trifluoroacetate (crude).

5.8 g (1.41 mMol) of Boc-Cys-Gly-Asn-Leu-Ser(-tBu)-Thr-(tBu)-Cys-Met-Leu-Gly-Thr(tBu)-Tyr(tBu)-Thr(tBu)-Gln-Asp(OtBu)-Phe-Asn-Lys(Boc)-Phe-His-Thr(tBu)-Phe-Pro-Gln-Thr(tBu)-Asn-Thr(tBu)-Gly-Val-Gly-Ala-Pro-NH(tBu)-Cys-Met-Leu-Gly-Thr-(tBu)-Thr(tBu)-Phe-Asn-Lys(Boc)-Phe-His-Thr(tBu)-Phe-Pro-Gln-Thr(tBu)-Asn-Thr(tBu)-Gly-Val-Gly-Ala-Pro-NH₂ is dissolved under nitrogen in 70 ml of 85% trifluoroacetic acid at 0°, and the solution is then stirred for two hours at 29°–31°. The solution is poured into 600 ml of ice-cooled and peroxide-free ether with vigorous stirring; the formed filtrate is filtered off and dried in high vacuum.

2. Asn²⁶-Thr²⁷-calcitonin M inner salt.

The dried precipitate obtained under 1. is dissolved in 130 ml of water, filtered through a G4 glass frit, and precipitated with diluted ammonia as follows: the solution is stirred under nitrogen at room temperature, with approx. 1N ammonia solution being slowly added dropwise (T = 0.97). The pH value is continuously measured with a glass electrode. The dropwise addition is regulated in such a manner that the pH assumes a value of 5 within about 1.5 hours. In the course of a further hour, a pH value of 6 is obtained by the continued addition of ammonia. During this period of time, the inner salt commences to precipitate. The dropwise addition of diluted ammonia solution is so maintained that within a further one hour a pH value of 7.6 is attained. Stirring is continued for a further three hours; filtration is then performed and the residue is well washed with water of pH 7.5 (adjusted by ammonia). The residue is subsequently dried in high vacuum.

3. Asn²⁶-Thr²⁷-calcitonin M-trihydrochloride.

The water-insoluble inner salt obtained under 2. is suspended in 80 ml of water/t-butanol 1:1. An addition is made of 39.0 ml of 0.1N hydrochloric acid, the whole is stirred for several minutes under nitrogen and filtered. Washing is subsequently repeatedly performed with a total amount of 120 ml of water/t-butanol (1:1), and lyophilisation is effected. There is obtained a colourless lyophilisate, which is equilibrated with the humidity in the atmosphere. Yield: 3.13 g. The product yields the following analytical values:

| | |
|---|---|
| thin-layer chromatogram on cellulose (Merck): | |
| | Rf = 0.41 in the system 114 |
| | 0.36 in the system 45 |
| | 0.55 in the system 101A |
| on aluminium oxide with 8% gypsum: | 0.49 in the system 52. |

The migration distance in thin-layer electrophoresis on cellulose plates (Merck) at pH 1.9 (formic acid)acetic acid buffer), 9 V/cm and 3,5 hours running time, is 4.8 cm

EXAMPLE 4

Pure Thr²⁷-calcitonin M-acetate 80 mg of crude Thr²⁷-calcitonin M, acetic acid salt, is dissolved in 5 ml of water; there is then added portionwise, with stirring, a total amount of 1.2 ml of Merck ion exchanger No. II, weakly basic, free amine form, and the pH value of the solution increases from the original 4.6 to 6.1. Stirring is maintained for a further 2 hours at room temperature, in the course of which a flaky precipitate separates out and the pH of the solution attains a value of 7.1. Stirring is continued for 30 minutes at this pH value: the precipitate and the ion exchanger are together filtered off with suction and thereafter well washed with water. The peptide is then separated from the ion exchanger by stirring of the mixture, whilst still moist, with 15 ml of 90% acetic acid with heating at 60°, and filtration under suction of the acetic acid solution. Lyophilisation of the eluate yields 74 mg of Thr²⁷-calcitonin M-acetate having a very high degree of purity. Rf value with thin-layer chromatography on cellulose plates in the system 52 = 0.50, Rf = 0.49 on aluminum oxide plates in the system 101A = 0.52.

In thin-layer electrophoresis (pH = 1.9; 280V, 2 hours), the product migrates 4.4 cm towards the cathode. Acetic acid content: 4.22% (gas-chromatographically); water content: 7.78% (Karl Fischer titration); peptide content: 87.4% (titrimetrically); UV-spectrum: $\lambda_{max} = 276$ nm; $\epsilon = 1560$ ($c = 2$ in 5% acetic acid, calculated on peptide content of 87.4%). Molar amino acid ratio after total hydrolysis (6-N. HCl, 24 hours, 110°) (calculated values in brackets): Lys: 0.93 (1); His : 0.95 (1): NH₃ : 3.40 (4); Asp : 3.00 (3); Thr : 5.23 (6); Ser : 1.17 (1); Gln : 2.02 (2); Pro : 2.06 (2); Gly : 3.87 (4); Ala : 2.03 (2); ½(Cys)₂ : 2.13 (2); Val : 1 (reference value); Met : 1.07 (1); Leu : 1.82 (2); Tyr: 0.99 (1): Phe : 3.06 (3).

EXAMPLE 5

Cys-Gly-Asn-Leu-Ser-Thr-Cys-Met-Leu-Gly-Thr-Leu-Thr-Gln-Asp-Phe-Asn-Lys-Phe-His-Thr-Phe-Pro-Gln-Thr-Asn-Thr-Gly-Val-Gly-Ala-Pro-NH₂, Acetate (Leu¹²-Asn²⁶-Thr²⁷-calcitonin M-acetate).

170 mg of Boc-Cys-Gly-Asn-Leu-Ser(tBu)-Thr(tBu)-Cys-Met-Leu-Gly-Thr(tBu)-Leu-Thr(tBu)-Gln-Asp(OtBu)-Phe-Asn-Lys(Boc)-Phe-His-Thr(tBu)-Phe-Pro-Gln-Thr(tBu)-Asn-Thr(tBu)-Gly-Val-Gly-Ala-Pro-NH₂ is dissolved in 5 ml of 90% trifluoroacetic acid, and the solution is left to stand for 90 minutes at 25°; the peptide-trifluoroacetate is precipitated with peroxide-free ether, filtered off with suction, rinsed with ether, dried, and dissolved in 1% acetic acid. The solution is filtered through a column of Merck ion exchanger (weakly basic acetate form) and eluted with 1% acetic acid, and the eluate (116 mg) is eluated. The resulting acetate is purified by dissolving it in 5 ml of water (pH of the solution =4.2) and adding portionwise, with stirring, a total amount of 2.8 ml of Merck ion exchanger No. II (weakly basic, base form). In the course thereof, the pH of solution slowly rises, and when it attains a value of about 6.7 the free peptide commences to precipitate. Stirring is carried out for a total of 2 hours, during which time a pH value of 7.1 is reached. The precipitate and the ion exchanger are filtered off together with suction, subsequently washed with water, and the peptide is then dissolved out of the ion exchanger by stirring with 90% acetic acid heated to 60°C. Filtration under suction is performed, the residue is washed with 90% acetic acid and lyophilised. The yield is 98 mg of $Leu^{12}$-$Asn^{26}$-$Thr^{27}$-calcitonin M in the form of acetate of high purity.
DC: Rf (101A) = 0.33;
DA: Rf (52) = 0.47.

EXAMPLE 6

Pure calcitonin M (acetate)

110 mg of crude cacitonin M-acetate is dissolved in 5 ml of water, and to the solution there is added portionwise in the course of 1 hour, with stirring, 1.0 ml of Merck-ion exchanger No. III strongly basic. During this time, the pH value of the solution increases to 6.6, and the precipitation of calcitonin commences. After continued stirring at room temperature, the pH value of the mixture increases further to 7.3 and remains constant there.

The ion exchanger and the precipitated peptide are then together filtered off with suction; the residue is subsequently washed with water, and the peptide is dissolved out of the ion exchanger by the addition of warm 90% acetic acid. Filtration with suction is again performed, and the residue is then washed with 90% acetic acid and lyophilised. There is thus obtaned calcitonin M-acetate of high purity; the analytical data thereof correspond to those of the product obtained in Example 1.

What we claim is:
1. Process for the purification of synthetically produced calcitonins having an isoelectric point which is between the pH values of approx. 5 to 10, wherein the calcitonin-peptide is precipitated as inner salt from an aqueous solution of a salt, said salt being soluble in water or in a solution of water and an organic peptide solvent, with acids or bases by adjustment of the pH to the isoelectric range.
2. Process according to claim 1, wherein the starting material used is a salt of calcitonin M.
3. Process according to claim 1, wherein the starting material used is a salt of an analog of calcitonin M.
4. Process according to claim 1, wherein the starting material used is a salt of a desamino[1] derivative of a calcitonin.
5. Process according to claim 1, wherein the starting material used is the crude peptide in the form of a hydrochloride.
6. Process according to claim 1, wherein the starting material used is the crude peptide in the form of a trifluoroacetate or of acetate.
7. Process according to claim 1, wherein the adjustment of the pH to the isoelectric range is attained by means of an inorganic acid or base.
8. Process according to claim 1, wherein the adjustment of the pH to the isoelectric range is attained by means of an ion exchanger.
9. Process according to claim 8, wherein the peptide is separated from the ion exchanger by conversion into a water-soluble salt.

* * * * *